United States Patent [19]

Singh et al.

[11] Patent Number: 5,608,064

[45] Date of Patent: Mar. 4, 1997

[54] PURINYL SALTS USEFUL FOR PREPARING GUANINE CONTAINING ANTIVIRAL AGENTS

[75] Inventors: Janak Singh; Gregory S. Bisacchi, both of Lawrenceville; Jollie D. Godfrey, Jr., Trenton; Toomas Mitt, Plainsboro; Richard H. Mueller, Ringoes; Robert Zahler, Pennington; Thomas P. Kissick, Lawrenceville, all of N.J.

[73] Assignee: Bristol-Myers Squibb Co., Princeton, N.J.

[21] Appl. No.: 457,183

[22] Filed: Jun. 1, 1995

Related U.S. Application Data

[60] Division of Ser. No. 7,950, Jan. 25, 1993, which is a continuation-in-part of Ser. No. 912,384, Jul. 13, 1992, abandoned.

[51] Int. Cl.$^6$ .................... C07D 473/40; C07D 473/18
[52] U.S. Cl. .................................. 544/277; 544/276
[58] Field of Search ........................... 544/277

[56] References Cited

U.S. PATENT DOCUMENTS

| | | | |
|---|---|---|---|
| 4,495,190 | 1/1985 | Hagberg et al. | 514/262 |
| 4,658,044 | 4/1987 | Ravenscroft | 549/415 |
| 5,059,690 | 10/1991 | Zahler et al. | 544/276 |
| 5,064,961 | 11/1991 | Bisacchi et al. | 544/276 |
| 5,126,345 | 6/1992 | Slusarchyk et al. | 514/254 |
| 5,153,352 | 10/1992 | Norbeck et al. | 560/17 |
| 5,314,893 | 5/1994 | Tino et al. | 544/277 |

FOREIGN PATENT DOCUMENTS

| | | |
|---|---|---|
| 55239 | 6/1982 | European Pat. Off. . |
| 278501 | 8/1988 | European Pat. Off. . |
| 352013 | 1/1990 | European Pat. Off. . |
| 358154 | 3/1990 | European Pat. Off. . |
| 366385 | 5/1990 | European Pat. Off. . |
| 458363 | 11/1991 | European Pat. Off. . |

OTHER PUBLICATIONS

Searcey et al., Synthetic Communications 19 (7 & 8), pp. 1309–1315 (1989).
Herdewijn, Antiviral Research, 19, pp. 1–14 (1992).
Bronson et al., Biorganic & Medicinal Chemistry Letters, vol. 2, No. 7, pp. 685–690 (1992).
Martin et al., Nucleosides & Nucleotides 8(5 & 6), pp. 923–926 (1989).
Bronson et al., J. Med. Chem., vol. 32, pp. 1457–1463 (1989).
Harden et al., J. Med. Chem., vol. 30, pp. 1636–1642 (1987).
Harden et al., J. Med. Chem., vol. 32, pp. 1738–1743 (1989).
Kim et al., J. Med. Chem., vol. 33, pp. 1207–1213 and 1797–1800(1990).
Borthwick et al., J. Chem. Soc., Chem. Commun. pp. 656–658 (1988).
Borthwick et al., Tetrahedron Letters, vol. 31, No. 5, pp. 767–770 (1990).
Parker et al., Molecular Pharmacology, vol. 41, pp. 245–251 (1992).
Shealy et al., J. Med. Chem., vol. 27, pp. 1416–1421 (1984).
Yu et al., J. Med. Chem., vol. 35, pp. 2958–2969 (1992).
Jenny et al., Nucelosides & Nucleotides, 11(6), pp. 1257–1261 (1992).
Hanna et al., J. Heterocyclic Chem., vol. 25, pp. 1899–1903 (1988).
Galynker et al., Tetrahedron Letters, vol. 23, pp. 4461–4464 (1982).
Okabe et al., Tetrahedron Letters, vol. 30, pp. 2203–2206 (1989).
Kugelman et al., J. Chem. Soc. Perkin I, pp. 1113–1126 (1976).
Fraser-Reid et al., J.A.C.S., vol. 92, pp. 6661–6663 (1970).
Greenspoon et al., J. Org. Chem., vol. 53, pp. 3723–3731 (1988).
Elion et al., Annals New York Academy of Sciences, vol. 255, pp. 468–480 (1975).
Beaman et al., J. Org. Chem., vol. 27, pp. 986–990 (1962).

*Primary Examiner*—Mark L. Berch
*Attorney, Agent, or Firm*—Stephen B. Davis

[57] ABSTRACT

A purine salt of the formula

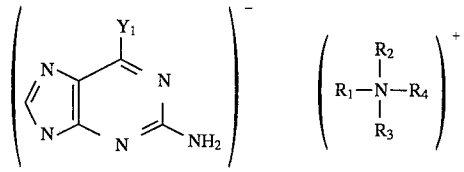

wherein $Y_1$ is chloro, bromo, or iodo, and $R_1$, $R_2$, $R_3$, and $R_4$ are independently selected from alkyl and substituted alkyl.

5 Claims, No Drawings

PURINYL SALTS USEFUL FOR PREPARING GUANINE CONTAINING ANTIVIRAL AGENTS

RELATED APPLICATION

This application is a division of Ser. No. 007,950 filed Jan. 25, 1993 which is a continuation-in-part of Ser. No. 912,384 filed Jul. 13, 1992, now abandoned.

BACKGROUND OF THE INVENTION

Antiviral agents having a guaninyl substituent on a carbohydrate surrogate are known. For example, the compound [1R- (1α,2β,3α)]-2-amino-9-[2,3-bis (hydroxymethyl)cyclobutyl]-1,9-dihydro-6H-purin-6-one, i.e.,

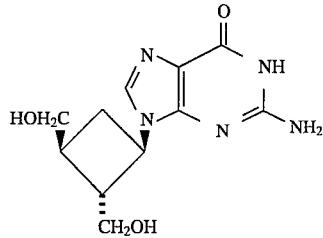

is an antiviral agent with activity against herpes simplex virus type 1 and 2, varicella zoster virus, human cytomeglavirus, vaccina virus, murine leukemia virus, and human immunodeficiency virus.

Bisacchi et al. in U.S. Pat. No. 5,064,961 disclose preparing this antiviral agent by reacting a bis(2,3-protected hydroxymethyl)cyclobutane of the formula

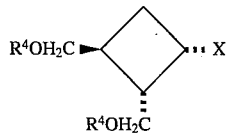

wherein X is a leaving group and $R^4$ is a protecting group with a protected guanine such as 2-amino-6-benzyloxypurine, 2-amino-6-methoxyethoxypurine, 2-amino-6-chloropurine, or 2-acetamido-6-hydroxypurine in the presence of a base such as potassium carbonate or sodium hydride in a solvent such as dimethylformamide at from about 40° C. to 150° C., preferably 100° to 120° C. for 4 to 48 hours. Removal of the $R^4$ protecting groups and the guanine protecting group yields the desired antiviral agent.

Slusarchyk et al. in U.S. Pat. No. 5,126,345 disclose a similar process to prepare the racemic compound (±)-(1α, 2β,3α)-2-amino-9- [2,3-bis(hydroxymethyl)cyclobutyl]-1, 9-dihydro-6H-purin-6-one.

Ichikawa et al. in European Patent Application 358,154 disclose reacting a cyclobutane of the formula

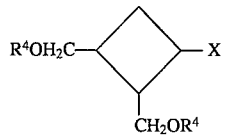

wherein X is a leaving group and $R^4$ is hydrogen or a protecting group with a nucleic acid base including 2-amino-6-chloropurine in the presence of a basic catalyst. Ichikawa disclose the preparation of [1R-(1α,2β,3α)]-2-amino-9-[2, 3-bis(hydroxymethyl)-cyclobutyl]-1,9-dihydro-6H-purin-6-one.

Norbeck et al. in U.S. Pat. No. 5,153,352 also disclose the preparation of [1R-(1α,2β,3α)]-2-amino-9-[2,3-bis(hydroxymethyl)- cyclobutyl]-1,9-dihydro-6H-purin-6-one.

Hagberg et al. in European Patent Application 55,239 and Zahler et al. in European Patent Application 458,363 disclose the tetrabutylammonium salt of 2-amino-6-benzyloxypurine.

SUMMARY OF THE INVENTION

This invention is directed to a process for preparing antiviral compounds of the formula (I)

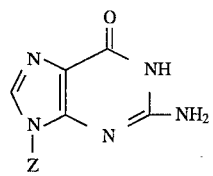

wherein Z is a carbohydrate surrogate by reacting a purine salt of the formula (II)

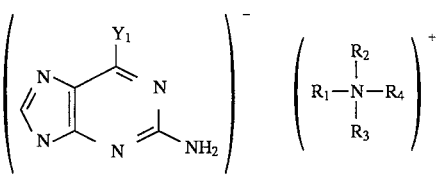

with the compound of the formula (III)

$$Z_1—X$$

to yield the purine of the formula (IV)

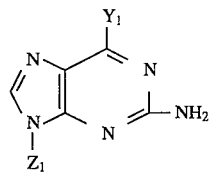

wherein x is a leaving group, $Z_1$ is a protected form of carbohydrate surrogate Z, $Y_1$ is iodo, bromo, or chloro, and $R_1$, $R_2$, $R_3$, and $R_4$ are independently straight or branched chain alkyl of 1 to 10 carbons or substituted straight or branched chain alkyl of 1 to 10 carbons. The compound of formula IV is then converted to the antiviral agent of formula I.

In the preferred process of this invention, the antiviral agent of formula I is [1R-(1α,2β,3α)]-2-amino-9-[2,3-bis(hydroxymethyl)cyclobutyl]-1, 9-dihydro-6H-purin-6-one and it is prepared by reacting a purine salt of formula II with the bis(2,3protected hydroxymethyl) cyclobutane of the formula (V)

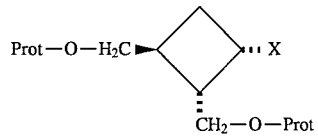

wherein Prot is a hydroxy protecting group. This reaction yields the cyclobutyl purine of the formula (VI)

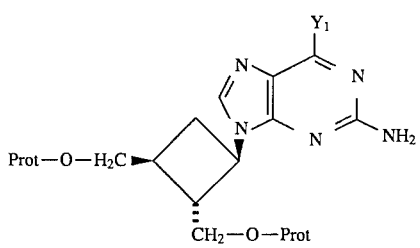

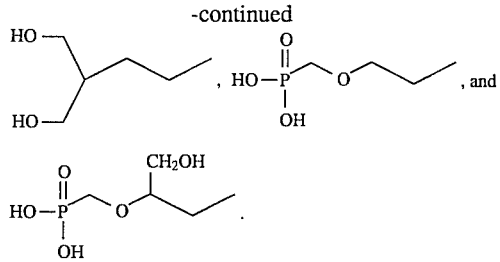

which is then converted to the antiviral agent [1R-(α,2β, 3α)]-2-amino-9-[2,3-bis(hydroxymethyl)-cyclobutyl]-1,9-dihydro-6H-purin-6-one.

The bis(2,3-protected hydroxymethyl)-cyclobutane of formula V is optically active, the relative sterochemistry of the substituent X is drawn to indicate that the leaving group X is cis to the vicinal—$CH_2$—O-Prot substituent and that the two —$CH_2$—O-Prot substituents are trans to each other.

This invention is also directed to the novel purine salts of formula I.

DETAILED DESCRIPTION OF THE INVENTION

The term "alkyl" refers to straight and branched chain groups of 1 to 10 carbons. The term "substituted alkyl" refers to such alkyl groups of 1 to 10 carbons having one, two or three substituents, preferably one, selected from alkoxy of 1 to 6 carbons and aryl. The term "aryl" refers to phenyl and phenyl having one, two, or three substituents, preferably one, selected from alkyl of 1 to 6 carbons, alkoxy of 1 to 6 carbons, chloro, bromo, iodo, and fluoro.

The carbohydrate surrogate Z includes cyclized and acyclic moieties which possess antiviral activity when substituted with a guanine moiety. Suitable groups for Z include

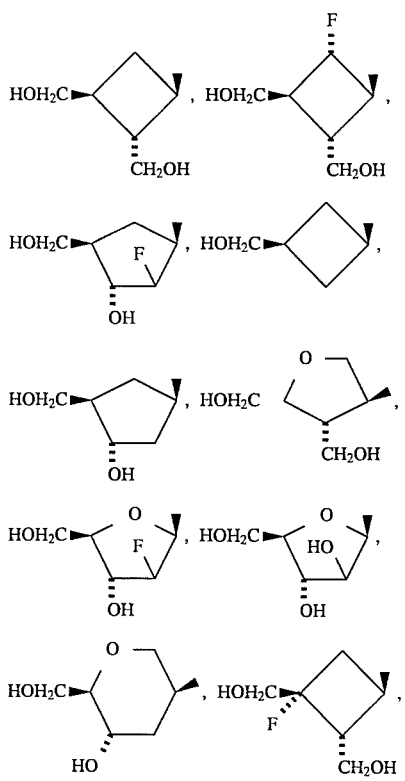

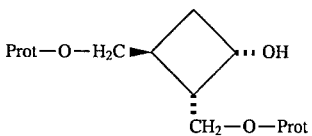

$Z_1$ represents the moiety Z wherein the hydroxy groups are protected. Suitable hydroxy protecting groups include hindered silyl groups such as t-butyldimethylsilyl, t-butyldiphenylsilyl, (triphenylmethyl)dimethylsilyl, methyldiisopropylsilyl and triisopropylsilyl, benzyl and substituted benzyl groups such as p-methoxybenzyl, acyl groups of the $$\begin{matrix} O \\ \| \\ -C-R_5 \end{matrix}$$

wherein $R_5$ is a straight or branched chain lower alkyl of 1 to 6 carbons, or phenyl, especially acetyl or benzoyl, trityl, and substituted trityl groups such as 4-monomethoxy trityl or 4,4'-dimethoxytrityl.

X in the compounds of formula III is a leaving group such as chloro, bromo, iodo, an aryl sulfonyloxy group such as p-toluenesulfonyloxy, an alkyl sulfonyloxy group such as methanesulfonyloxy, a substituted alkyl sulfonyloxy group, preferably a perfluoroalkanesulfonyloxy group such as trifluoromethanesulfonyloxy, a nitro-substituted benzene sulfonyloxy group such as p-nitrobenzenesulfonyloxy, or fluorosulfonyloxy.

The compounds of formula III are prepared according to known procedures or as set forth below. For example, the bis(2,3-protected hydroxymethyl)-cyclobutane of formula V can be prepared as taught by Bisacchi et al. in U.S. Pat. No. 5,064,961. For example, when X is a perfluoroalkane sulfonyloxy group such as trifluoromethanesulfonyloxy, the perfluoroalkanesulfonic anhydride such as trifluoromethanesulfonic anhydride is reacted with the diprotected 2,3- hydroxymethyl cyclobutanol of the formula (VII)

in an inert solvent such as methylene chloride or chloroform, preferably methylene chloride, in the presence of a base such as pyridine or triethylamine, preferably pyridine. The reaction can be run at from about −20° C. to the boiling point of the solvent, preferably at about 0° C. to room temperature.

When X is a nitro-substituted benzene sulfonyloxy group such as p-nitrobenzenesulfonyloxy, the cyclobutanol of formula VII is reacted with a nitro-substituted benzene sulfonating reagent such as p-nitrobenzenesulfonyl chloride in pyridine or in an inert solvent such as methylene chloride or chloroform containing a base such as pyridine or triethylamine.

When X is fluorosulfonyloxy, the cyclobutanol of formula VII is reacted with fluorosulfonic anhydride in pyridine or in an inert solvent such as methylene chloride or chloroform containing a base such as pyridine or triethylamine.

The compounds of formula III

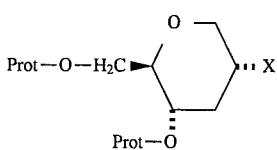

can be prepared from the pyran of the formulas (VIII)

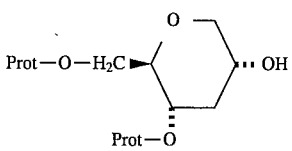

or (IX)

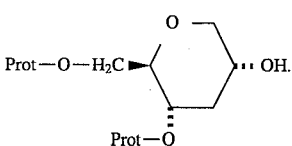

For example, treatment of the compound of formula VIII with p-toluenesulfonyl chloride in pyridine, or methanesulfonyl chloride and triethylamine, or trifluoromethanesulfonic anhydride and pyridine affords the corresponding compounds of formula III wherein X is p-toluenesulfonyloxy, methanesulfonyloxy, or trifluoromethanesulfonyloxy, respectively.

Alternatively, these compounds of formula III wherein X is p-toluenesulfonyloxy can also be prepared from the isomeric compound of formula IX by known methods [see I. Galynker et al., Tetrahedron Letters, 23, 4461(1982)]. For example, treatment of compound IX with diethyl or diisopropyl azodicarboxylate in the presence of triphenylphosine, and zinc p-toluenesulfonate affords the compound of formula III wherein X is p-toluenesulfonyloxy. Alternatively, these compounds of formula III wherein X is p-toluenesulfonyloxy or methanesulfonyloxy can also be prepared from the compound of formula IX by treatment with p-toluenesulfonic acid or methanesulfonic acid, respectively, in the presence of triethylamine, triphenylphosine, and diethyl or diisopropyl azodicarboxylate in a solvent such as toluene, ether, or dioxane.

These compounds of formula III wherein X is chloro, bromo, or iodo can be prepared by treating a compound of formula IX with a methyltriphenoxyphosphonium halide or methyltriphenylphosphonium halide (i.e., chloride, bromide, or iodide) in a solvent such as dimethylformamide. Alternatively, these compounds of formula III wherein X is chloro, bromo, or iodo can be prepared from the compound of formula IX using triphenylphosphine, diethyl or diisopropyl azodicarboxylate, and a source of halide such as methyl iodide, methyl bromide, or methylene chloride according to methodology known in the art. See, for,example, H. Loibner et al., Helv. Chim. Acta., 59, 2100 (1976).

The compounds of formulas VIII and IX can be prepared from the known compound of formula X [See M. Okabe et al., Tetrahedron Letters, 30, 2203 (1989); M. Kugelman et al., J. Chem. Soc. Perkin I, 1113(1976); B. Fraser-Reid et al., J. Amer. Chem. Soc., 92, 6661(1970) for the preparation of the compound of formula X] as outlined below:

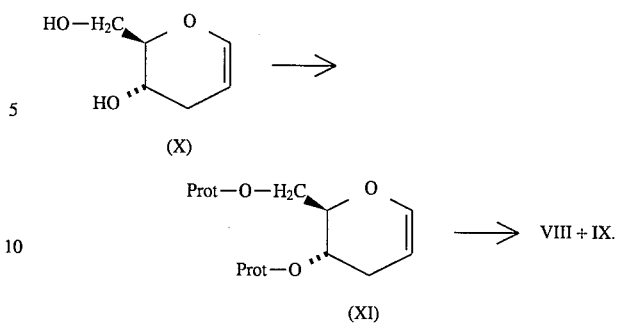

Treatment of the compound of formula X with various hydroxyl protecting reagents known in the art affords the compounds of formula XI.

The compound of formula XI wherein the hydroxy protecting groups are acetyl can also be obtained by the direct reduction of tri-O-acetyl-D-glucal, i.e.

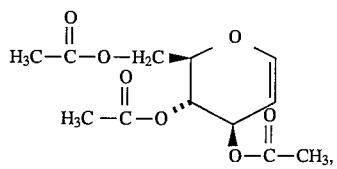

see N. Greenspoon et al., J. Org. Chem., 53, 3723 (1988). Alternatively, this compound of formula XI can also be obtained by treatment of tri-O-acetyl-D-glucal with sodium borohydride in the presence of Cu(I)Br and tetrakis(triphenylphosphine)-palladium(O) in an aprotic solvent such as tetrahydrofuran and/or dimethoxyethane.

Hydroboration of the compound of formula XI with borane-tetrahydrofuran complex followed by treatment with aqueous sodium bicarbonate and 30% hydrogen peroxide affords a mixture of the compound of formula VIII and the isomeric compound of formula IX which can be separated, e.g., by chromatography on silica gel.

The compounds of formula III

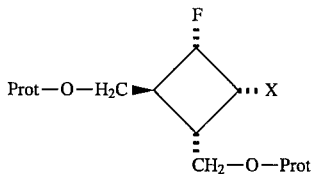

are taught by Zahler et al. in European Patent Application 458,363.

The compounds of formula III

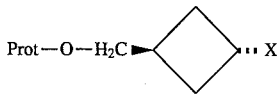

are taught by Slusarchyk in European Application 52,013.

The compounds of formula III

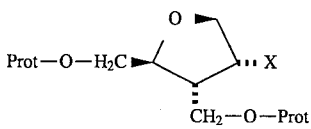

are taught by Zahler et al. in U.S. Pat. No. 5,059,690.

The compounds of formula III

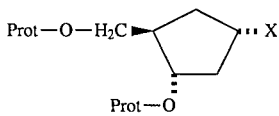

are taught by Ravenscroft in U.S. Pat. No. 4,658,044.
The compounds of formula III

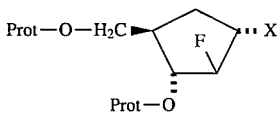

and

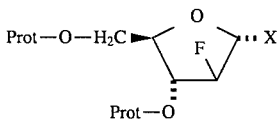

are taught by Borthwick et al., J. Chem. Soc. Chem. Commun., 1988, p. 656–658.

The compounds of formula III

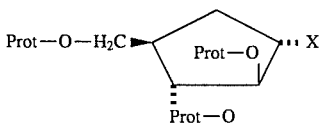

are taught by Hanna et al., J. Heterocyclic Chem., Vol. 25, p. 1899–1903 (1988).

Similarly, the acyclic compounds of formula III are taught in the literature as note Martin et al., Nucleosides & Nucleotides, Vol. 8, p. 923–926 (1989); Bronson et al., J. Med. Chem., Vol. 32., p. 1457–1463 (1989); Harden et al., J. Med. Chem., Vol. 30, p. 1636–1642 (1987) and J. Med. Chem., Vol. 32, p. 1738–1743 (1989); and Kim et al., J. Med. Chem., Vol. 33, p. 1207–1213 (1990) and J. Med. Chem., Vol. 33, p. 1797–1800 (1990).

The purine salts of formula II are prepared by reaction of a purine compound of the formula (XII)

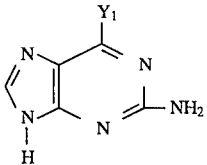

with a compound of the formula (XIII)

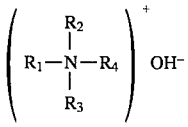

in a solvent such as ethanol or methylene chloride and water followed by isolation of the salt from the reaction, The purine compound of formula XII wherein $Y_1$ is chloro is commercially available or can be prepared by known methods. The purine of formula XII wherein $Y_1$ is bromo can be prepared by the procedure described by A. G. Beaman et al., J. Org. Chem., 27, 986 (1962). The compound of formula XII wherein $Y_1$ is iodo can be prepared by treatment of the compound of formula XII wherein $Y_1$ is chloro with aqueous hydroiodic acid at about 1° C.

The compounds of formula XIII are known in the art and are either commercially available or can be prepared by published methods.

The reaction between the purine salt of formula II and the compound of formula III is run in an aprotic solvent such as methylene chloride, acetonitrile, acetone, tetrahydrofuran, and the like at a temperature of from about –20° to 100° C. for from about 30 minutes to about 24 hours, preferably from about one hour to about 12 hours. When X is a perfluoroalkanesulfonyloxy group such as trifluoromethylsulfonyloxy, the solvent employed is preferably methylene chloride and the reaction is run at from about 0° C. to about 30° C. When X is a nitro-substituted benzenesulfonyloxy group such as p-nitrobenzenesulfonyloxy, the solvent employed is preferably acetonitrile and the reaction is run at from about 30° C. to about 90° C.

The resulting intermediate of formula IV is converted to the desired antiviral agent of formula I by selective removal of the hydroxy protecting group or groups in $Z_1$ and conversion of the $Y_1$ group to a 6-oxo. For example, when the hydroxy protecting group or groups in the compound of formula IV are acyl treatment with catalytic sodium methoxide in methanol yields the compound of the formula (XIV)

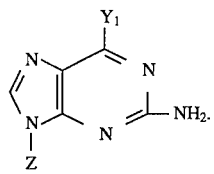

Similarly, when the hydroxy protecting group or groups in the compound of formula IV are hindered silyl groups treatment with fluoride ion such as tetrabutylammonium fluoride yields the compound of formula XIV and when the hydroxy protecting group or groups in the compound of formula IV are benzyl or substituted benzyl treatment with boron trichloride yields the compound of formula XIV. Acid hydrolysis of the compound of formula XIV such as by using hot aqueous hydrochloric acid gives the desired 6-oxo antiviral agent of formula I.

Alternatively, treatment of the compound of formula IV wherein the hydroxy protecting group or groups are acyl, benzyl, or substituted benzyl with hot aqueous acid effects selective conversion of the $Y_1$ group to a 6-oxo group to provide a compound of the formula (XV)

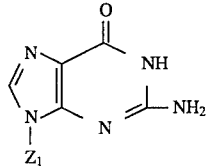

wherein the hydroxy group or groups in $Z_1$ are protected by an acyl, benzyl, or substituted benzyl. In this reaction, when the protecting group or groups are acyl and $Y_1$ is iodo treatment of the compound of formula IV with hot aqueous acetic acid yields the compound of formula XV. When the hydroxy protecting group or groups are benzyl or substituted benzyl and $Y_1$ is chloro, bromo or iodo treatment of the compound of formula IV with hot aqueous hydrochloric acid yields the compound of formula XV. The hydroxy protecting group or groups can then be removed from the compound of formula XV by the methods described above or other known methods in the art to give the desired antiviral agents of formula I. For example, when the hydroxy protecting group or groups are an acyl such as benzoyl treatment with aqueous sodium hydroxide or sodium methoxide in methanol will give the desired final product. Similarly, when the hydroxy protecting group or groups is benzyl or substituted benzyl hydrogenolysis will give the desired product.

In a further alternate procedure, the compound of formula XIV or the hydroxy protected compound of formula IV wherein the protecting group or groups are acyl can be treated with excess sodium methoxide in methanol at reflux to provide a compound of the formula (XVI)

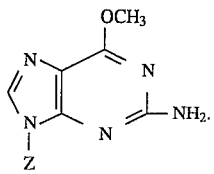

Acid hydrolysis, for example, using hot aqueous hydrochloric acid, of the compound of formula XVI gives the desired 6-oxo antiviral agent of formula I.

Alternatively, treatment of a compound of formula IV wherein the hydroxy protecting group or groups are acyl with hot aqueous hydroxide such as sodium or potassium hydroxide or with an acid such as hydrochloric acid followed by sodium or potassium hydroxide and heating gives the desired 6-oxo antiviral agent of formula I.

Preferably, the process of this invention employs the compounds of formula III wherein $Z_1$—X is

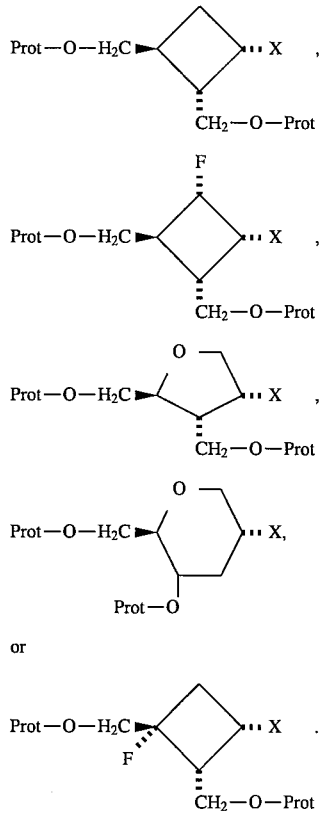

Prot is acetyl or benzoyl.

X is p-nitrobenzenesulfonyloxy or trifluoromethanesulfonyloxy.

Preferred purine salts of formula I for use within the process of this invention are those wherein:

$Y_1$ is chloro or iodo, especially iodo.

$R_1$, $R_2$, $R_3$ and $R_4$ are each n-butyl or $R_1$, $R_2$, and $R_3$ are ethyl and $R_4$ is benzyl.

This preferred process, particularly when $Z_1$—X is

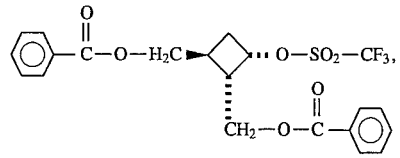

can be performed under milder reaction conditions, in a shorter period of time, and with higher yields than previously reported process for preparing the antiviral agents of formula I.

The following examples are illustrative of the invention.

EXAMPLE

[1R-(1α,2β,3α)]-2-Amino-9-[2,3-bis(hydroxymethyl)cyclobutyl]-1,9-dihydro-6H-purin-6-one a) 6-Iodo-9H-purin-2-amine 6-Chloro-9H-purin-2-amine (5.0 g., 29.5 mmole) was added to 47% hydrogen iodide (61 ml., 12.2 ml./g.) chilled in an ice bath. After 1.5 hours, water (61 ml.) was added and the mixture stirred in an ice-bath for 30 minutes. The yellow solid was filtered out and the filter cake was washed with water. The wet solid was transferred to a beaker and the residue in the funnel was washed into the beaker with water (30 ml.). 6M Sodium hydroxide (7 ml.) was added with stirring until all the solid had dissolved (pH 14). The solution was added to boiling water (30 ml.) containing acetic acid (3 ml.). The mixture was boiled briefly and allowed to stand at room temperature for one hour. The product was filtered off, washed with water, and dried under vacuum overnight to give 6.88 g. of the desired product; m.p. about 240° C. (dec.).

Anal. calc'd. for $C_5H_4N_5I \cdot 0.014\ H_2O$: C, 22.99; H, 1.55; N, 26.81; I, 48.57; $H_2O$, 0.10 Found: C, 23.32; H, 1.52; N, 26.75; I, 48.14; $H_2O$, 0.09 b) 6-Iodo-9H-purin-2-amine, ion (1–), triethyl-(phenylmethyl) ammonium(1:) salt

Benzyltriethylammonium hydroxide (24.6 ml., 43.3 mmole, 40 wt % in methanol) was added to a suspension of 6-iodo-9H-purin-2-amine (10.0 g., 38.3 mmole) stirred in absolute ethanol (22 ml.) until nearly all of the suspension had dissolved. Additional 6-iodo-9H-purin-2-amine (0.4 g.) was added and the mixture was stirred for 15 minutes. The excess 6-iodo-9H-purin-2-amine was filtered off, washed with absolute ethanol, and the filtrate evaporated until no more ethanol was observed on the condenser. The residue was rapidly stirred while ethyl acetate (25 ml.) was added all at once. A solution was formed from which a solid precipitated. Additional ethyl acetate (175 ml.) was added dropwise over 30 minutes. After precipitation was complete, the mixture was stirred for 2 hours, filtered, washed with ethyl acetate, and dried under vacuum to give 15.16 g. of the desired salt product; m.p. 156°–159° C. (effervescent).

Anal. calc'd. for $C_{18}H_{25}N_5I \cdot 0.065\ H_2O$. 0.02 starting material: C, 47.39; H, 5.54; N, 18.63; I, 28.22; $H_2O$, 0.26 Found: C, 47.45; H, 5.50; N, 18.89; I, 27.94; $H_2O$, 0.26.

c) [1S-(1α,2β,3α)]-3-(2-Amino-6-iodo-9H-purin-9-yl)-1,2-cyclobutanedimethanol, dibenzoate ester Trifluoromethanesulfonic anhydride (4.02 ml., 24.0 mmole) in dry methylene chloride (4 ml.) was added dropwise over 5 minutes to a solution of [1S-(1α,2β,3β)]-3-hydroxy-1,2-cyclobutane-dimethanol, dibenzoate ester (6.80 g., 20.0 mmole) and pyridine (2.56 ml., 30.0 mmole) in methylene chloride (30 ml.) chilled in an ice-bath. After 20 minutes, the reaction was quenched with ice, washed into a separatory funnel with methylene chloride, and washed with cold water (2×30 ml.), 5% sodium bisulfate (30 ml.), and water (30 ml.). Each aqueous layer was rinsed with a few mls. of methylene chloride which were added to the previous layer. The methylene chloride layer was dried with magnesium sulfate with stirring for 5 minutes. The mixture was filtered and the magnesium sulfate was washed three times with methylene chloride. The total volume of the methylene chloride filtrate was about 75 ml. (about 0.25M in trifluoromethane-sulfonate).

6-Iodo-9H-purin-2-amine, ion (1⁻), triethyl(phenylmethyl)ammonium (1:1) salt (10.49 g., 22.0 mmole) was added and the suspension was stirred at room temperature. After 6 hours the mixture was filtered, the filter cake was washed with methylene chloride, and the filtrate evaporated. The residue was taken up in water (50 ml.) and ethyl acetate (100 ml.). The aqueous layer was separated, and the ethyl acetate layer was washed with water (3×50 ml.), 30% phosphoric acid (2×10 ml.), water (50 ml.), a mixture of 5% aqueous sodium bicarbonate (30 ml.) and brine (20 ml.), and brine (10 ml.). The organic layer was dried over magnesium sulfate for 5 minutes and 10 g. of charcoal (Dacro, fine mesh) was added. The mixture was stirred for 15 minutes, filtered through Celite, and the filter cake was washed 5 times with ethyl acetate. The filtrate was evaporated to a foam (11.67 g.). The residue was evaporated from a mixture of methylene chloride (10 ml.) and absolute ethanol (10 ml.) to form a solid. This solid was heated on the steam bath to boiling with absolute ethanol (80 ml., 7 ml./g. foam) for 2 minutes. The mixture was kept at room temperature for 3 hours, filtered, and washed twice with cold 95% ethanol. The solid was dried under vacuum overnight to give 8.07 g. of the desired product; m.p. 148°–149° C., $[\alpha]_D = -20.5°$ (c=1, chloroform). TLC (silica gel, ethyl acetate, $R_f=0.65$).

Anal. calc'd. for $C_{25}H_{22}IN_5O_4 \cdot 0.06\ H_2O \cdot 0.02\ C_2H_5OH$: C, 51.38; H, 3.83; N, 11.96; I, 21.68; $H_2O$, 0.18 Found: C, 51.19; H, 3.77; N, 11.89; I, 21.86; $H_2O$, 0.18.

d) [1R-(1α,2β,3α)]-2-Amino-9-[2,3-bis(hydroxymethyl)cyclobutyl]-1,9-dihydro-6-one A solution of sodium methoxide (5.3 ml., 3.9M prepared from sodium/methanol) was added by syringe to a suspension of [1S-(1α,2β,3α)]-3-(2-amino-6-iodo9H-purin-9-yl)-1,2-cyclobutanedimethanol, dibenzoate ester (8.0 g., 13.7 mmole) in dry methanol (40 ml.). The mixture was refluxed for 1.5 hours. The solution was neutralized with 1N HCl (10.1 ml.) to pH 7. The methanol was evaporated to give a reaction mixture containing [1S-(1α,2β,3α)]-3-(2-amino-6-methoxy-9H-purin-9yl)-1,2-cyclobutanedimethanol.

This aqueous mixture was washed into a separatory funnel with water (2×8 ml.) and acidified with concentrated HCl (3.6 ml., 43.9 mmole) to pH of about 0.5. The mixture was washed with methylene chloride (3×15 ml.) to remove methylbenzoate and the aqueous layer was rotary evaporated for a few minutes to remove any residual methylene chloride. The aqueous layer was heated in a 95° oil bath for 3 hours. Sodium hydroxide (10.6 ml., 4N) was added to adjust the pH to 7. Crystals formed immediately. The mixture was allowed to cool to room temperature slowly. After standing overnight at room temperature, the mixture was chilled at 0° C. for one hour, filtered, and washed with cold water. The wet product was washed into a 250 ml. flask with 35 ml. of water. The mixture was heated to boiling and 30 ml. of water was added to dissolve all of the product. The solution was kept at room temperature for 3 hours and at 0° C. for one hour. The crystals were filtered, washed with cold water, and dried under vacuum over phosphorus pentoxide to give 3.4 g. of the desired product; m.p. about 290° C. (dec.), $[\alpha]_D= -24.4°$ (c=1, dimethylsulfoxide), +25.3° (c=1, 0.1 N sodium hydroxide). TLC (silica gel; tetrahydrofuran, methanol, ammonium hydroxide, 6:3:1, $R_f=0.45$).

Anal. calc'd. for $C_{11}H_{15}N_5O_3 \cdot 1.04\ H_2O$: C, 46.51; H, 6.06; N, 24.65; $H_2O$, 6.60 Found: C, 46.71; H, 6.02; N, 24.88; $H_2O$, 6.62.

EXAMPLE 2

[1S-(1α,2β,3α)]-3-(2-Amino-6-iodo-9H-purin-9-yl)-1,2-cyclobutanedimethanol, dibenzoate ester a) 6-Iodo-9H-purin-2-amine, ion (1 –), tetrabutylammonium (1:1) salt 6-Iodo-9H-purin-2-amine (133 g., 510 mmole) ground up in a mortar and pestle was washed into a 2 liter pot with 1.5 liter dichloromethane. Aqueous tetrabutylammonium hydroxide (1.53M, 333 ml., 510 mmole) was added and the mixture was stirred mechanically for 30 minutes. The mixture was then filtered through Celite, washed five times with methylene chloride, and the methylene chloride layer was separated, dried (MgSO₄), and evaporated. The residue was evaporated from toluene (300 ml.). The residue was taken up in 1 liter of ethyl acetate and heated briefly to form a two-phase mixture. This mixture was stirred mechanically at room temperature for 30 minutes. The resulting crystals were filtered, washed with ethyl acetate, and dried under vacuum overnight to give 213.5 g. of product. 20 g. of this material was dried further overnight at 50° C. under vacuum over phosphorus pentoxide to give 6-iodo-9H-purin-2-amine, ion (1⁻), tetrabutylammonium (1:1) salt; m.p. 114°–116° C.

Anal. Calc'd. for $C_5H_3IN_5 \cdot C_{16}H_{36}N \cdot 0.13\ H_2O$: C, 49.96; H, 7.84; N, 16.65; I, 25.14; $H_2O$, 0.46 Found: C, 50.17; H, 7.91; N, 16.86; I, 25.33; $H_2O$, 0.48.

b) [1S-(1α,2β,3α)]-3-(2-Amino-6-iodo-9H-purin-9-yl)-1,2-cyclobutanedimethanol, dibenzoate ester

[1S-(1α,2β,3β)]-3-Hydroxy-1,2-cyclobutanedimethanol, dibenzoate ester (3.40 g., 10.0 mmole) was dissolved in methylene chloride (15 ml.) and chilled in an ice bath. Pyridine (1.28 ml., 15.0 mmole) was added. Trifluoromethanesulfonic anhydride (2.01 ml., 12.0 mmole) was added by syringe to methylene chloride (3 ml.) in a dropping funnel. The trifluoromethanesulfonic anhydride solution was added dropwise to the cold reaction mixture over 5 minutes. After a total of 25 minutes, the reaction was worked up at a temperature below 20° C. The reaction mixture was quenched with ice and diluted to 100 ml. with methylene chloride. The organic layer was washed with 25 ml. of each of ice-water (twice), cold 5% sodium bisulfate, and ice water. Each organic layer was backwashed with 2 ml. of methylene chloride. The combined organic layers were dried over magnesium sulfate. After filtration, the solution was evaporated down to a mobile oil in a bath of ice water.

6-Iodo-9H-purin-2-amine, ion (1⁻), tetrabutylammonium (1:1) salt (6.02 g., 12 mmole, dried over phosphorus pentoxide under vacuum at 50° C., 0.13M% water) was dissolved in methylene chloride (7 ml.) and chilled in an ice bath. The above trifluoromethanesulfonyloxy material was washed into this solution with methylene chloride (5×1 ml.). After 30 minutes, the ice bath was removed and the reaction mixture was stirred overnight at room temperature. A precipitate formed. The methylene chloride was evaporated and the residue was taken up in ethyl acetate (50 ml.) by brief heating on a steam bath. The mixture was diluted with toluene (50 ml.), washed with 30% phosphoric acid (25 and 10 ml.), and water (6×150 ml.). The organic layer was then washed with 5% sodium bicarbonate (50 ml.) and brine (50 ml.) and then dried (magnesium sulfate). Charcoal (Darco, 5 g.) was added to the dry solution, stirred for 30 minutes, and filtered through Celite. The filter cake was washed with ethyl acetate (5×10 ml.). The filtrate was evaporated to give 5.51 g. of crude product.

The residue was heated to boiling with absolute ethanol (90 ml.) on the steam bath. The product formed an oil on heating which crystallized in the boiling mixture. The hot mixture was allowed to cool to room temperature and allowed to stand for 4 hours and then kept at 0° C. overnight. The crystals were filtered, washed with cold 95% ethanol (2×20 ml.), and dried under vacuum to give 4.43 g. of material, m.p. 148°–149° C.

This material (1.0 g.) was dissolved in methylene chloride (3 ml.) and diluted with absolute ethanol (10 ml.). The solution was evaporated under vacuum until it had become cloudy. It was heated briefly on the steam bath and kept at room temperature for 2 hours. After being kept at 0° C. overnight, the product was filtered, washed twice with cold 95% ethanol, and dried under vacuum to give 0.946 g. of the desired product; m.p. 149°–150° C., $[\alpha]_D$=−20.5° (c=1, chloroform). TLC (silica gel; ethanol, $R_f$=0.59).

Anal. calc'd. for $C_{25}H_{22}IN_5O_4 \cdot 0.13\ H_2O\ 0.15\ C_2H_5OH$: C, 51.28; H, 3.94; N, 11.82; I, 21.41; $H_2O$, 0.4 Found: C, 51.46; H, 3.75; N, 11.76; I, 21.09; $H_2O$, 0.4.

EXAMPLE 3

[1S-(1α,2β,3α)]-3-(2.amino-6-methoxy-9H-purin9-yl)-1,2-cyclobutanedimethanol

An analytically pure sample of this intermediate was prepared as follows.

A suspension of [1S-(1α,2β,3α)]-3-(2-amino-6-iodo-9H-purin-9-yl)-1,2-cyclobutanedimethanol, dibenzoate ester (2.915 g., 5 mmole) and sodium methoxide (0.35 ml., 4.63M in methanol, 1.62 mmole) in methanol (20 ml.) was stirred under nitrogen at room temperature. After 3.5 hours a clear solution was obtained. After 4.5 hours, sodium methoxide (1.5 ml., 4.63M in methanol, 6.9 mmole) was added and the mixture was heated at 65° C. for 5 hours. The mixture was cooled to room temperature and acetic acid was added (0.48 g., 8 mmole, pH about 8.5 measured with electrode and about 5 with wet pH paper). The solvent was evaporated under vacuum and the residue was heated in acetone (15 ml.) and filtered. The insoluble material was washed with acetone (5 ml.). The solvent was removed from the filtrate and the residue was washed three times with hexane (5 ml.). The insoluble portion was redissolved in hot acetone (15 ml.). The product crystallized out. After standing overnight in an ice bath, the solid was filtered, washed with acetone (5 ml.), and dried under vacuum over phosphorus pentoxide for three hours to give 1.04 g. of crude product. After 2 days a second crop (0.236 g.) of product was obtained from the mother liquors. These two crops were combined and 1.236 g. of impure product was dissolved in hot ethyl acetate (15 ml.). Silica gel (EM-60, 60 g.) was added and the solvent was removed on a rotary evaporator. This adsorbed material was then charged on a silica gel column (about 25×250 mm) and eluted successively with ethyl acetate (100 ml.), 10% ethanol in ethyl acetate (1700 ml.), and 20% ethanol in ethyl acetate (1100 ml.). The TLC homogeneous fractions were combined and the solvent was removed to give 0.7 g. of the desired product. The solid was heated in acetone (15 ml.) and allowed to stand at room temperature for 7 hours. The product was filtered, washed with acetone and dried over phosphorus pentoxide under vacuum for 15 hours to give 0.55 g. of the desired product; m.p. 144°–145° C.; $[\alpha]_D$=−21.4° (c=1, dimethylsulfoxide). TLC(silica gel; ethanol:hexane, 1:1, $R_f$=0.5).

Anal. calc'd. for $C_{12}H_{17}N_5O_3$: C, 51.61; H, 6.13; N, 25.07 Found: C, 51.52; H, 6.07; N, 25.28.

EXAMPLE 4

[1R-(1α,2β,3α)]-2-Amino-9- [2,3-bis(hydroxymethyl)-cyclobutyl]-1,9-dihydro-6H-purin-6-one a) 6-Chloro-9H-purin-2amine, ion(1⁻), tetrabutylammonium (1:1) salt An aqueous solution of tetrabutylammonium hydroxide (1.53M, 2.5 ml., 3.83 mmole) was added dropwise to a slurry of 6-chloro-9H-purin-2-amine (1.69 g., 10 mmole) in methylene chloride (40 ml.) at ambient temperature. After 10 minutes the biphasic solution was filtered with suction through a sintered glass funnel to remove a small amount of undissolved solid. The filtrate was transferred to a separatory funnel and the organic layer was separated, dried over magnesium sulfate, and filtered. The filtrate was evaporated under vacuum and the residue was triturated with ethyl acetate (20 ml. ) and filtered. The product was dried under vacuum over phosphorus pentoxide at ambient temperature for 5 hours to give 3.41 g. of desired product; m.p. greater than 89° C.

Anal. calc'd. for $C_{21}H_{39}N_6Cl \cdot 0.65\ H_2O$: C, 59.66; H, 9.61, N, 19.88; Cl, 8.39; $H_2O$, 2.79 Found: C, 59.22; H, 9.88, N, 19.86; Cl, 8.74; $H_2O$, 2.77.

b) [1S-(1α,2β,3α)]-3-(2Amino-6-chloro-9H-purin-9-yl)-1,2-cyclobutanedimethanol, dibenzoate ester A solution of trifluoromethanesulfonic anhydride (5.97 ml., 35.5 mmole) in dry methylene chloride (10 ml. ) was added dropwise over 5 minutes to a solution of [1S-(1α,2β,3β)]-3-hydroxy-1,2-cyclobutanedimethanol, dibenzoate ester (10.06 g., 29.6 mmole) and pyridine (3.7 ml., 44.4 mmole) in methylene chloride (45 ml. ) chilled in an ice bath. After 20 minutes the reaction was quenched with ice, washed into a separatory funnel with methylene chloride, and washed with ice cold water (2×100 ml.), 5% sodium bisulfate (150 ml.), and ice cold water (100 ml.). Each aqueous layer was washed with methylene chloride (10 ml.) which was added to the previous methylene chloride layer. The slightly colored and turbid methylene chloride layer was dried with magnesium sulfate by stirring for 20 minutes and filtered to give an almost clear solution. The solvent was evaporated to 25 ml. and then the solution was diluted to 101 ml. with dry methylene chloride to give a 0.29 molar solution of trifluoromethanesulfonyloxy compound. The solution was stored over magnesium sulfate under argon at −20° C.

6-Chloro-9H-purin-2-amine, ion (1⁻), tetrabutylammonium (1:1) salt (2.47 g., 6 mmole) was added to the above trifluoromethanesulfonyloxy compound (17.2 ml., 0.29M in methylene chloride, 5 mmole) and the suspension was stirred at room temperature. After 6 hours the reaction flask was stored at −20° C. overnight. After warming to room temperature, the mixture was filtered. Baker silica gel (60–200 mesh, 10 ml.) was added to the filtrate and the solvent was evaporated under vacuum. The solid was charged on a silica gel column (25×260 mm., prepared in 25% ethyl acetate in hexane). The product was eluted successively with 25%, 50%, and 75% ethyl acetate in hexane (100 ml. each) and ethyl acetate (300 ml.) collecting 50 ml. fractions. Fractions 9–12 (TLC, silica gel, ethyl acetate, Rf=0.56) were combined and evaporated to give 1.54 g. of desired product.

c) [1S-(1α,2β,3α)]-3-(2-Amino-6-chloro-9H-purin-9-yl)-1,2-Cyclobutanedimethanol

A solution of sodium methoxide (0.39M in methanol, 0.081 ml., 0.32 mmole) was added by syringe to a suspension of [1S-(1α,2β,3α)]-3-(2-amino-6-chloro-9H-purin-9-yl)-1,2-cyclo-butanedimethanol, dibenzoate ester (1.54 g., 3.14 mmole) in dry methanol (20 ml.). After stirring for 2 hours at room temperature the mixture was stored for 2 days at −20° C. The product crystallized during further stirring at room temperature for 2 hours. The mixture was allowed to stand at 0° C. for 3 hours. The solid was filtered, washed with cold methanol, and dried under vacuum to give 0.52 g of desired product; m.p. 198–201° C. TLC (silica gel; ethanol:ethyl acetate, 1:9, $R_f$=0.49).

Anal. calc'd. for $C_{11}H_{14}ClN_5O_2$: C, 46.43; H, 4.99; N, 24.61; Cl, 12.46; $H_2O$, 0.30 Found: C, 46.81; H, 5.01; N, 24.24; Cl, 12.54; $H_2O$, 0.36.

d) [1R-(1α,2β,3α)]-2-Amino-9-[2,3-bis (hydroxymethyl)-cyclobutyl]-1,9-dihydro-6H-purin-6-one A mixture of [1S-(1α,2β,3α)]-3-(2-amino-6-chloro-9H-purin-9-yl)-1,2-cyclobutanedimethanol and 2N HCl was heated under nitrogen at 95° C. After one hour the mixture was neutralized with 4N sodium hydroxide (about 0.6 ml.) and a few drops of 1N sodium hydroxide to a pH of about 8.0. A thick white precipitate formed. The mixture was stirred in an ice bath for about 1.5 hours, filtered, washed with ice cold water (2 ml.), and dried over phosphorus pentoxide under vacuum to give the desired product.

EXAMPLE 5

[1S-(1α,2β,3α)]-3-(2-Amino-6-iodo-9H-purin-9-yl)-1,2-cyclobutanedimethanol, dibenzoate ester a) [1S-(1α,2β,3β)]-3-[[(4-Nitrophenyl)-sulfonyl]-oxy]-1,2-cyclobutanedimethanol, dibenzoate ester p-Nitrobenzenesulfonylchloride (5.9 g., 24.0 mmole) was added to a solution of [1S-(1α,2β,3β)]-3-hydroxy-1,2-cyclobutanedimethanol, dibenzoate ester 6.8 g., 20.0 mmole) in pyridine (20 ml.). After stirring overnight at room temperature, water (8 ml.) was added and the mixture was stirred for one hour. The pyridine was evaporated off and the residue was treated with ethyl acetate (150 ml.). The mixture was washed successively with water, 1% hydrochloric acid, water, 5% sodium bicarbonate, water, and brine. The solution was dried (MgSO$_4$), stirred for 15 minutes with activated charcoal, and filtered through Celite. The solvent was evaporated to give 8.7 g. of crude product. This crude solid was triturated with ether (25 ml.) and then stirred for one hour. The product was filtered, washed with ether, and dried under vacuum to give 7.89 g. of [1S-(1α,2β,3β)]-3[[(4-nitrophenyl)sulfonyl]oxy]-1,2-cyclobutanedimethanol, dibenzoate ester; m.p. 100°–101° C.

Anal. calc'd. for $C_{26}H_{23}NO_9S$ . 0.11 $H_2O$: C, 59.19; H, 4.44; N, 2.65; S, 6.08; $H_2O$, 0.39 Found: C, 59.17; H, 4.02; N, 2.61; S, 6.19; $H_2O$, 0.39.

b) [1S-(1α,2β,3α)]-3-(2-Amino-6-iodo-9H-purin-9-yl)-1,2-cyclobutanedimethanol, dibenzoate ester 6-Iodo-9H-purine-2-amine, ion (1$^-$), triethyl-(phenylmethyl)ammonium (1:1) salt (4.97 g., 11.0 mmole) was added to a solution of the product from part (a) (5.25 g., 10.0 mmole) in acetonitrile (20 ml.) and the mixture was refluxed for 8.5 hours. The solvent was evaporated and the residue was taken up in ethyl acetate (200 ml.). The solution was washed with water (4×200 ml.), dried (MgSO$_4$), and the solvent was evaporated. The crude product was purified by flash chromatography over silica gel (25×200 mm. column). The product was eluted successively with 500 ml. each of 10%, 30%, 60%, and 80% ethyl acetate in hexane followed by ethyl acetate (500 ml.). Product containing fractions were combined and evaporated to give 3.73 g. of desired product.

EXAMPLE 6

[1R-(1α,2β,3α)]-2-Amino-9-[2,3-bis(hydroxymethyl)-cyclobutyl]-1,9-dihydro-6H-purin-6-one a) [1R-(1α,2β,3α)]-2-Amino-9-[2,3-bis[(benzoyloxy)methyl]cyclobutyl]-1,9 -dihydro-6H-Durin-6-one A mixture of [1S-(1α,2β,3α)]-3-(2-amino-6-iodo-9H-purin-9-yl)-1,2-cyclobutanedimethanol, dibenzoate ester (1.755 g., 3.0 mmole) and 57% aqueous acetic acid was heated to 100° C. under a nitrogen atmosphere. After 4.5 hours, the solution was cooled and treated with sodium bicarbonate (252 mg., 3.0 mmole). The solvent was evaporated on a rotary evaporator and the residue was dried for one hour under vacuum. The solid was treated with water (10 ml.), filtered, and washed with water. The product was dried under vacuum overnight. The solid was slurried in aqueous sodium bicarbonate (10 ml.). After stirring for 45 minutes, the solid was filtered, washed with water, and dried under vacuum over phosphorus pentoxide to give 1.4 g. of crude product.

A solution of the crude product in ethyl acetate was charged on a silica gel column (200 ml., prepared in hexane). The column was eluted successively with 100 ml. of ethyl acetate, 1.5 l. 10% methanol in ethyl acetate, and 500 ml. of 50% methanol in ethyl acetate. Fractions were collected (about 35 ml. each) as soon as the yellow band on the column started to elute. Fractions 3 to 17 gave 1.1 g. of product as a light yellow solid. An analytical sample was obtained by crystallization from ethyl acetate followed by recrystallization from acetone/water to give pure product; m.p. 160°–161° C.; [α]$_D$=−11.5° (c=1, dimethylformamide). TLC (silica gel; methanol: methylene chloride, 1:9, $R_f$=0.43).

Anal. calc'd. for $C_{25}H_{23}N_5O_5$. 0.5 $H_2O$: C, 62.23; H, 5.01; N, 14.52; $H_2O$, 1.87 Found C, 62.00; H, 4.68; N, 14.56; $H_2O$, 1.59.

b) [1R-(1α,2β,3α)]-2-Amino-9-[2,3-bis(hydroxy-methyl)cyclobutyl]-1,9-dihydro-6H-purin-6-one A suspension of the product from part (a) (95 mg., 0.2 mmole) in aqueous sodium hydroxide (1 ml., 1N) was heated under argon at 100° C. in an oil bath. After 3 hours, the mixture was cooled to room temperature and acidified with 1N hydrochloric acid to pH 3. Benzoic acid partly crystallized out during acidification. The mixture was washed with methylene chloride (3×2 ml.) to remove the benzoic acid. The pH of the aqueous layer was adjusted to 6 with 1N sodium hydroxide. The aqueous solution (total volume about 7 ml.) was concentrated to about 4 ml. on a rotary evaporator. The product was crystallized out during evaporation. The flask was cooled in an ice bath. After 3 hours, the product was filtered, washed with ice-cold water and dried over phosphorus pentoxide under vacuum to give 48 mg. of desired product as white crystals; m.p. greater than 280° (dec.).

Alternatively, the desired final product was also prepared as follows:

A suspension of the product from part (a) (95 mg., 0.2 mmole) in methanolic sodium methoxide (2 ml., 0.2M) was refluxed under argon in an oil bath. After 2.5 hours, the mixture was cooled to room temperature and the solvent was evaporated. The residue was treated with 1.5 ml. of 1N hydrochloric acid. The mixture was washed with methylene chloride (3×2 ml.) to remove methyl-benzoate. The pH of the aqueous layer was adjusted to 6 with 1N sodium hydroxide. The product crystallized out in a few minutes. The flask was cooled in an ice bath. After 3 hours, the product was filtered, washed with ice cold water, and dried over phosphorous pentoxide under vacuum overnight to give 42 mg. of product as pale yellow crystals; m.p. 275° (dec.).

EXAMPLE 7

[3S-(3α,5β,6α)]-2-Amino-1,9-dihydro-9-[tetrahydro-5-hydroxy-6 -(hydroxymethyl)-2H-pyran-3-yl]-6H-purin-6-one a) (2R-trans)-3-(Acetyloxy)-3,4-dihydro-2H-pyran-2-methanol, acetate (ester)

A suspension of sodium borohydride (3.14 g., 83.0 mmole) in anhydrous tetrahydrofuran (226 ml.) and 1,2-dimethoxyethane (113 ml.) was refluxed for 1.5 hours. After cooling, copper (I) bromide (297 mg., 2.07 mmole) was added and the mixture was refluxed for 2 hours. To this slurry was added tri-O-acetyl-D-glucal (11.30 g., 41.53 mmole) and tetrakis-(triphenyl-phosphine) palladium (O) (2.39 g., 2.076 mmole) at room temperature. The mixture was stirred at room temperature overnight, and then heated at 50° C. for 5 hours. The reaction mixture was then cooled to room temperature, treated at 0° C. with saturated sodium bicarbonate (11 ml.) and 30% hydrogen peroxide (22 ml.). The reaction mixture was diluted with ethyl acetate, washed with saturated sodium bicarbonate, dried and concentrated in vacuo. The residue was purified by column chromatography on silica gel, eluting with ethyl acetate (5% to 10%)hexane with 0.1% triethylamine to give the title compound as a white solid (2.18 g., 10.18 mmole).

b) [2R-(2α,3β,5β)]-2-[(Acetyloxy)methyl]tetrahydro-2H-pyran-3,5-diol, 3-acetate

A 1.0M borane-tetrahydrofuran complex (9.59 ml., 9.59 mmole) was added dropwise at 0° C. under nitrogen to a dry tetrahydrofuran solution (22 ml.) of the product from part (a) (2.055 g., 9.59 mmole). After 2.5 hours, the mixture was treated with saturated sodium bicarbonate (9 ml.) and 30% hydrogen peroxide (4.3' ml.) at 0°–5° C. and stirred for 2 hours. The reaction mixture was cooled to 0° C., diluted with ethyl acetate, washed with sodium bicarbonate, dried and concentrated in vacuo. The crude product was purified by column chromatography on silica gel, eluting with ethyl acetate (50%, 75%)-hexane, to yield the title compound as a colorless oil (0.654 g., $R_f$=0.44) and the epimeric alcohol, [2R-(2α,3β,5α)]-2-[(acetyloxy)-methyl]tetrahydro-2H-pyran-3,5-diol, 3-acetate, as a white crystalline solid (0.325 g., $R_f$=0.34).

c) [2R-(2α,3β,5α)]-3-(Acetyloxy)-5-(2-amino-6-iodo-9H-purin-9-yl)tetrahydro-2H-pyran-2-methanol, acetate (ester)

To a mixture of 6-iodo-2-aminopurine (1.21 g., 4.637 mmole) in methylene chloride (12 ml.) at room temperature, was added 1.5M tetra (n-butyl) ammonium hydroxide (2.7 ml., 4.05 mmole). The reaction mixture was stirred for 10 minutes, and the volatiles were removed in vacuo. Methylene chloride (12 ml.) was added to the white residue, and the resulting solution was dried (magnesium sulfate), filtered, and the filtrate was concentrated in vacuo to yield the tetra (n-butyl) ammonium salt of 6-iodo-2-aminopurine as a white residue.

To a stirred solution of [2R-(2α,3β,5β)]-2[(acetyloxy)methyl]tetrahydro-2H-pyran-3,5-diol, 3-acetate (0.633 g., 2.72 mmol) in methylene chloride (12 ml.) at −20° C. was added pyridine (0.33 ml., 4.09 mmole) and trifluoromethanesulfonic anhydride (0.504 ml., 3.0 mmole). The reaction was warmed to room temperature. The mixture was diluted with methylene chloride, washed with 10% sulfuric acid, saturated sodium bicarbonate, and water. The organic layer was separated, dried, and concentrated in vacuo to yield crude trifluoromethanesulfonyl product as a dark pink oil.

A solution of this trifluoromethanesulfonyl product in methylene chloride (4 ml.) was added to a mixture of the tetra (n-butyl) ammonium salt of 6-iodo-2-aminopurine in methylene chloride (10 ml.) and the reaction was stirred at room temperature for 16 hours. The mixture was concentrated in vacuo. The residue was dissolved in ethyl acetate (120 ml.) and water (120 ml.), treated for 2 hours with AG-MP 50 cation resin (sodium⁺ form, 30 g.), and filtered through Celite®. The crude product was purified by column chromatography on silica gel, eluting with ethyl acetate (50%, 75%, 100)-hexane, to yield the title compound as a foamy yellow solid (0.587 g., 1.235 mmole).

d) [3S-(3α,5β,6α)]-2-Amino-1,9-dihydro-9[tetrahydro-5-hydroxy-6-(hydroxymethyl)-2H-pyran-3-yl]-6H-purin-6-one Sodium methoxide solution (0.43M, 4.22 ml.) was added to a solution of the product from part (c) (0.58 g., 1.2 mmole) in methanol (5 ml.). The mixture was stirred at room temperature for 45 minutes and then refluxed for 5 hours. After cooling to room temperature, the pH of the mixture was adjusted to 7.0 by the addition of 1N hydrochloric acid (1.4 ml.), and concentrated in vacuo. Additional 1N hydrochloric acid (2.5 ml.) was added to the residue and this mixture was heated at 50° C. for 18 hours and then at 85° C. for 3 hours. The reaction mixture was cooled to room temperature, diluted with water, and the pH adjusted to 7.0 by the addition of 3N sodium hydroxide (0.8 ml.). The mixture was concentrated in vacuo and the residue was subjected to a CHP-20 column, eluting with a continuous gradient (water to 25% acetonitrile in water), to afford a yellow residue. This crude product was triturated in methylene chloride, recrystallized from hot water, and treated with activated charcoal to yield 48 mg. of the title compound as white crystals; $[\alpha]_D$=−3.46° (c=0.0866, dimethylsulfoxide). $^1$H NMR (270MHz, DMSO-$d_6$):δ10.57 (s, 1H, -NH); (s,1H,C8H); 6.47 (s,2H,-NH$_2$); 4.92 (d, J=5.28 Hz, 1H); 4.67–4.62 (t,J=5.86 Hz, 1H); 4,52 (s,1H); 4.06 (d,J=2.34 Hz,1H); 3.83–3.78 (dd,J=2.34 Hz, 12.3 Hz, 1H); 3.66 (m, 1H); 3.5 (m, 1H); 3.16 (m, 1H); 2.51 (m, 1H); 2.20 (m, 1H); 1.85–1.79 (m, 1H). I.R. (KBr pellet): 3435, 3194, 2648, 2903, 1697, 1639, 1606, 1398, 1180, 1066 cm$^{-1}$.

Anal. calc'd. for $C_{11}H_{15}N_5O_4$.0.36 H$_2$O: C, 45.90; H, 5.51; N, 24.33 Found: C, 46.07; H, 5.06; N, 24.16.

EXAMPLE 8

[3S-(3α,4β,5α)]-2-Amino-1,9-dihydro-9-[tetrahydro-4,5-bis(hydroxymethyl)-3-furanyl]-6H-purin-6-one a) [3S-(3α,4β,5α)]-6-Iodo-9-[tetrahydro-4,5-bis[(phenylmethoxy)methyl]-3 -furanyl]-9H-purin-2-amine A mixture of [3R-(3α,4α,5β)]-tetrahydro-4,5-bis[(Phenylmethoxy)methyl]-3-furanol, 4-methyl-benzenesulfonate ester (54.24 g., 112.5 mmole, prepared as described in Example 1 of U.S. Pat. No. 5,059,690) and 6-iodo-9H-purin-2-amine, ion (1⁻), tetrabutylammonium (1:1) salt (89.1 g., 177.5 mmole ) in anhydrous dimethylformamide (600 ml. ) was heated under nitrogen at 85°–90° C. for 12 hours. The yellow solution was partitioned between water (1.5 l.) and ethyl acetate (1.5 l.). The organic layer was dried (sodium sulfate) and evaporated to give 66 g. of an oil. Chromatography on 5 l. of silica gel (K-60) in ethyl acetate/hexane (2/1) afforded 31.2 g. of the product ($R_f$=0.42, ethyl acetate/hexane, 2/1), which gave a crystalline product on standing; m.p. 84°–86° C.

b) [3S-(3α,4β,5α)]-6-Methoxy-9-[tetrhyro-4,5-bis[(phenylmethoxy)methyl]-3-furanyl]-9H-purin-2-amine A solution of the product from part (a) (31.2 g., 54.64 mmole) in warm methanol (500 ml.) was treated all at once with 10% sodium hydroxide (50 ml.), and then was heated for one hour on a steam cone. The pH was adjusted to 7 with 10% hydrochloric acid (45 ml.) and the mixture was evaporated to a gum. This was partitioned between ethyl acetate and water, the organic layer was dried (sodium sulfate), and evaporated to give 24.9 g. of product as a foam. TLC (silica gel; ethyl acetate) $R_f$=0.57.

c) [3S-(3α,4β,5α)]-6-Methoxy-9-[tetrahydro-4,5bis(hydroxymethyl)-3-furanyl]-9H-purin-2-amine All of the product from part (b) was covered with 95% ethanol (800 ml.), 20 g. of 20% palladium hydroxide on carbon catalyst was added, followed by cyclohexene (400 ml.). The mixture was refluxed at 85°–90° C. for 2 hours. The catalyst was filtered on Celite® and the filter cake was washed with methanol (300 ml.). The filtrate was evaporated to give 17.8 g. of the product as an oil. TLC (silica gel; chloroform:methanol:ammonium hydroxide, 6:3:1) $R_f$=0.75.

d) [3S-(3α,4β,5α)]-2-Amino-1,9-dihydro-9[tetrahydro-4,5-bis(hydroxmethyl)-3-furanyl]-6H-purin-6-one All of the crude product from part (c) was dissolved in 1N hydrochloric acid (200 ml.) and heated at 70°–75° C. for 10 hours under nitrogen. The resulting solution was cooled to room temperature and filtered through a Celite® pad. The filtrate was basified to pH of about 8 by the addition of 20 ml. of concentrated ammonium hydroxide. The resulting white slurry was heated on a hot plate until dissolved, then allowed to come to room temperature over 2 hours. The mass of solid was filtered and washed with water (75 ml.), dried as much as possible, and the filter cake was washed with 200 ml. of acetonitrile and finally with 200 ml. of ether. Drying in vacuo gave 11.6 g. of solid, m.p. 240°–245° C., which was 99% pure by electrochromatography. This material was combined with 1.1 g. of product from a smaller run and recrystallized by dissolving in hot water (200 ml.), filtering hot (rapidly), and cooling to room temperature in an ice-bath. The solid was filtered and washed with 100 ml. of cold water. Drying in vacuo over phosphorus pentoxide for 18 hours gave 10.96 g. of product as a white solid; m.p. 270°–275° C. $[\alpha]_D$=–46.8° (c=0.22, dimethylsulfoxide).

Anal. calc'd. for $C_{11}H_{15}N_5O_4 \cdot 0.23H_2O \cdot 0.088NH_4Cl$: C, 45.54; H, 5.49; N, 24.57; Cl, 1.08 Found: C, 45.54; H, 5.40; N, 24.23; Cl, 1.08.

What is claimed is:

1. A compound of the formula

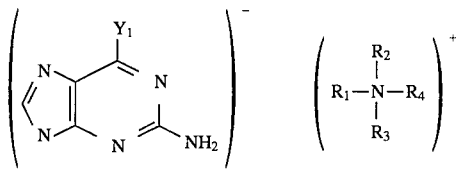

wherein:

$Y_1$ is chloro, bromo, or iodo;

$R_1$, $R_2$, $R_3$, and $R_4$ are independently selected from the group consisting of straight or branched chain alkyl of 1 to 10 carbons and substituted straight or branched chain alkyl of 1 to 10 carbons;

substituted straight or branched chain alkyl of 1 to 10 carbons refers to such alkyl groups having one, two, or three substituents selected from the group consisting of alkoxy of 1 to 6 carbons and aryl;

aryl refers to phenyl and phenyl having one, two, or three substituents selected from the group consisting of alkyl of 1 to 6 carbons, alkoxy of 1 to 6 carbons, chloro, bromo, iodo, and fluoro.

2. A compound of claim 1 wherein:

$Y_1$ is chloro or iodo;

$R_1$, $R_2$, $R_3$ and $R_4$ are each n-butyl or $R_1$, $R_2$, $R_3$ are each ethyl and $R_4$ is benzyl.

3. The compound of claim 2 wherein $Y_1$ is iodo; and $R_1$, $R_2$, $R_3$, and $R_4$ are each n-butyl.

4. The compound of claim 2 wherein $Y_1$ is iodo; and $R_1$, $R_2$, and $R_3$ are each ethyl and $R_4$ is benzyl.

5. The compound of claim 2 wherein $Y_1$ is chloro; and $R_1$, $R_2$, $R_3$, and $R_4$ are n-butyl.

* * * * *